United States Patent [19]

Quash et al.

[11] Patent Number: 4,853,326

[45] Date of Patent: Aug. 1, 1989

[54] CARBOHYDRATE PERTURBATIONS OF VIRUSES OR VIRAL ANTIGENS AND UTILIZATION FOR DIAGNOSTIC PROPHYLACTIC AND/OR THERAPEUTIC APPLICATIONS

[75] Inventors: Gerard A. Quash, France Ville, France; John D. Rodwell, Yardley; Thomas J. McKearn, New Hope, both of Pa.; Jean P. Ripoll, Chassieu, France

[73] Assignee: Cytogen Corporaton, Princeton, N.J.

[21] Appl. No.: 928,631

[22] Filed: Nov. 18, 1986

[30] Foreign Application Priority Data

Nov. 25, 1985 [FR] France .................. 85 17377

[51] Int. Cl.$^4$ ............... G01N 33/531; G01N 33/569; G01N 33/571; G01N 33/576
[52] U.S. Cl. ........................... 435/5; 435/7; 436/507; 436/510; 436/511; 436/518; 436/543; 436/548; 436/812; 436/820
[58] Field of Search ............ 435/5, 7; 436/507, 812, 436/820, 510, 511, 543, 548

[56] References Cited

U.S. PATENT DOCUMENTS

| | | | |
|---|---|---|---|
| 4,195,265 | 4/1980 | Koprowski | 424/85 |
| 4,217,338 | 8/1980 | Quash | 435/543 |
| 4,355,102 | 10/1982 | Quash | 435/5 |
| 4,367,309 | 1/1983 | Kondo et al. | 424/85 |
| 4,419,444 | 12/1983 | Quash | 435/7 |
| 4,604,348 | 8/1986 | Neurath | 436/518 |
| 4,634,666 | 1/1987 | Englemann et al. | 435/68 |

FOREIGN PATENT DOCUMENTS

| | | |
|---|---|---|
| 0088695 | 9/1983 | European Pat. Off. |
| 0117657 | 5/1984 | European Pat. Off. |
| 0122841 | 10/1984 | European Pat. Off. |
| 0156559 | 9/1982 | Japan |
| 84/04327 | 11/1984 | World Int. Prop. O. |
| 86/03224 | 6/1986 | World Int. Prop. O. |

OTHER PUBLICATIONS

Glorioso et al, *Virology*, 126, 1–16, 1983.
Berman et al, *Trends in Biochem*, 3, 51–53, 1985.
Finegold et al, *Bailey and Scott's Diagnostic Microbiology*, 5th Ed., C. V. Mosby Company, Saint Louis, 1978, pp. 272–278.
Dreesman et al, *Virology*, 69, 700–709, 1976.
Hagenaars et al, *Journ. Virol. Meth.*, 6, 233–239, 1983.
Krech et al, *Z. Immun.-Forsch., Bd.*, 141, 411–429, 1971.
Lee et al, *Prod. Natl. Acad. Sci.*, 81, 3856–3860, 1984.
Peake et al, *Chem. Abstr.*, 96, 214032t, 1982.
Bosch et al, *Chem. Abstr.*, 96, 214039a, 1982.
Quash, *Chem. Abstr.*, 90, 148119z, 1979.
Wang et al, *Proc. Natl. Acad. Sci.*, 83, 6159–6163, 1986.
Elder et al, *Journ. of Virology*, 57, 340–342, 1986.

*Primary Examiner*—Robert J. Warden
*Assistant Examiner*—David A. Saunders
*Attorney, Agent, or Firm*—Pennie & Edmonds

[57] ABSTRACT

Novel and improved methods for diagnosis, prognosis, prophylaxis and therapy of viral infections are described. The novel methods employ a virus, viral antigen or fragment thereof in which "perturbation" of an oligosaccharide moiety renders the virus, viral antigen or fragment thereof more specifically recognizable or reactive with neutralizing antibody. As described, "perturbation" of an oligosaccharide moiety encompasses any modification that (1) alters the chemical or physical structure of a carbohydrate residue that is naturally present; (2) that removes, wholly or in part, a carbohydrate residue; and/or (3) that prevents or alters addition of a carbohydrate residue. A variety of methods for oligosaccharide "perpetuation" are also described.

18 Claims, No Drawings

CARBOHYDRATE PERTURBATIONS OF VIRUSES OR VIRAL ANTIGENS AND UTILIZATION FOR DIAGNOSTIC PROPHYLACTIC AND/OR THERAPEUTIC APPLICATIONS

TABLE OF CONTENTS

1. Field of The Invention
2. Background of The Invention
3. Summary of The Invention
4. Detailed Description of The Invention
   4.1. Oligosaccharide Perturbations
   4.2. Applications
      4.2.1. Diagnostic and Prognostic Applications
         4.2.1.1. Dissociation of Immune Complexes
      4.2.2. Prophylactic and Therapeutic Applications
   4.3 Viruses and Viral Antigens
   Examples: Determination of Neutralizing Antibodies in Fruified Human lgG From Sera
5.1. Detection of Neutralizing Anti-CMV Anitbodies in Human IgG
5.2. Reproducibility of Neutralizing Antibody Titer
6. Example: Detection of Neutralizing Antibodies in Serum Samples
7. Example: Perturbation of Oligosaccharide Moiety of Virus and Attachment of Virus To a Solid Support

1. FIELD OF THE INVENTION

The present invention relates generally to novel and improved methods for diagnosis, prophylaxis and therapy of viral infections. More particularly the invention relates to novel methods employing a virus, viral antigen or fragment thereof in which an oligosaccharide moiety is perturbed in such a way that the virus, viral antigen or fragment thereof is specifically recognized by or reacts specifically with neutralizing antibodies. The term "perturbed" oligosaccharide moiety is intended to encompass any modification (1) that alters the chemical or physical structure of a carbohydrate residue that is naturally present; (2) that removes, wholly or in part, a carbohydrate residue that is naturally present; and/or (3) that prevents or alters the addition of a carbohydrate residue (i.e. prevents or alters glycosylation).

The perturbed viruses, viral antigens and fragments thereof prepared according to the present invention are useful for in vitro diagnostic and prognostic applications as well as for in vivo prophylactic and therapeutic applications.

2 BACKGROUND OF THE INVENTION

Viruses are important etiological agents of a wide variety of diseases. In animals the immune response comprises one of the basic mechanisms to fight viral infections. Classically, the immune response encompasses two facets: the B-lymphocyte antibody response, referred to as humoral immunity and a T-lymphocyte-mediated response, known as cell-mediated immunity. The present application is concerned particularly with the antibody response.

While specific antibody of classes IgG, IgM and IgA can bind to any accessible epitope on a surface protein of a virion, only those antibodies which bind with reasonably high avidity to particular epitopes on a particular protein in the outer capsid or envelope are capable of neutralizing the infectivity of the virion. These are termed "neutralizing antibodies." "Neutralization" as used throughout the instant specification is intended to include not only (1) classical virus neutralization which results when antibody binds to a surface antigen of a virion which ordinarily binds to a receptor on the surface of a susceptible cell and thereby prevents infection of a susceptible cell or leads to opsonization but also includes (2) interactions such as the binding of an antibody to neuraminidase of influenza virus (IF) which results in inhibition of release of progeny virus particles from the plasma membrane of infected cells and slows virus spread and (3) binding of an antibody to fusion protein (F) of paramyxoviruses which does not prevent initiation of infection but does block the direct cell to cell spread of newly formed virions once infection has been established. Antibodies directed against irrelevant or inaccessible epitopes of surface proteins, or against internal proteins of the virion, or virus-coded nonstructural proteins, such as virus-encoded enzymes can sometimes exert indirect immunopathological effects, but may play no role in elimination of the infection. These are "non-neutralizing antibodies." In fact, certain non-neutralizing antibodies not only form damaging circulating "immune complexes" but may actually impede access of neutralizing antibody and enhance the infectivity of the virion for some cells. For example, in the presence of sub-neutralizing concentration of neutralizing antibody or excess of non-neutralizing antibodies viruses such as togaviruses are actually taken up more efficiently by macrophages (via Fc receptors on the macrophage to which the virus-antibody complex binds). The virus multiples intracellulary to high titer inside the macrophages. Hence the non-neutralizing antibodies act as "enhancing antibody." Specific examples of such viruses include dengue virus types 1-4.

Thus in response to a viral infection, two very different kinds of antibodies are produced: neutralizing antibodies and non-neutralizing antibodies. Each is present in the serum of infected individuals or individuals previously exposed to a virus or a viral antigen in varying amounts. In order to assess the true immunocompetent status of an individual it is necessary to know the absolute and relative amounts of both neutralizing and non-neutralizing antibodies. Yet conventional serological assays of antiviral antibodies do not, and in fact cannot, distinguish these two kinds of antibodies. Conventional serological assays measure the presence of both types of antibodies. Hence there is no serological method for measuring or assessing the true immune status or immunocompetence of individuals.

The only conventional method for assessing virus neutralizing ability of serum of individuals has been the virus neutralization assay such as that described by Krech et al., Z. Immuno., Forsch. Bd. 141 S: 411-29 (1971). Neutralization assays require: (1) use of infectious virus and (2) cell culture techniques. Such assays are slow, cumbersome, labor intensive and expensive. Hence there has been a long-felt need for a rapid, inexpensive accurate serological method to assess the immunocompetent status of individuals.

Examples of specific situations in which a rapid, easy test for assessing the immunocompetence of an individual is particularly important include, but are not limited to, the following. Firstly, exposure of a pregnant female to a virus such as rubella virus or cytomegolovirus poses significant risk of congenital defects for the fetus. Using conventional serological methods such as ELISA assays the titer of all IgM and IgG antibodies against the relevant virus, both neutralizing and non-neutralizing, may be determined. If the total IgM level is elevated indicating that the response is due to reaction by a presumably "naive" immune system, a therapeutic abortion will be recommended because it is unlikely that neutralizing antibodies against the virus are present. If, however, only the total IgG level is elevated, no therapeutic abortion will be recommended because the test cannot distingush whether the IgG's present are neutralizing or non-neutralizing antibodies. The patient is faced with a long stress-filled pregnancy which may end in a child with congenital defects. Secondly, exposure of (or reactivation of previous infection associated with immunosuppression) organ transplant or bone marrow transplant patients to viruses such as cytomegalovirus (CMV) poses significant risks of clinical disease states including pneumonia, hepatitis, retinitis, encephalitis, etc. Moreover, the glomerulopathy induced by CMV adversely affects the survival of kidney grafts, so that renal transplant patients face additional life-threatening organ rejection [see generally, White et al., eds., in Medical Virology, 3d ed., Academic Press, Inc., New York, pp. 419-426 (1986)]. Thirdly, viral infections pose significant, indeed often life-threatening risks for immuno-suppressed patients including cancer patients undergoing chemotherapy, and those afflicted with either congenital or acquired immunodeficiency such as acquired immune deficiency syndrome (AIDS). Fourthly, certain viral infections endemic to specific geographic areas pose significant risks, for example, for military or diplomatic personnel stationed in these areas. Specific examples include but are not limited to Rift Valley fever, dengue etc. Vaccines may protect by actively eliciting the production of neutralizing antibodies. Evaluation of the immunocompetent status of personnel to be sent to these areas following vaccination is important.

In all the above examples, there is a need for rapid, serological methods for determining both the presence and titer of virus neutralizing antibodies. Examples of formats useful in such rapid, serological methods include but are not limited to Enzyme-Linked Immunosorbent Assays (ELISA), radioimmunoassays (RIA), immunofluoresence or other fluorescence-based assays, agglutination assays, etc.

Hagenaars et al., J. Virol. Methods 6: 233-39 (1983) described a modified inhibition ELISA assay which showed some correlation between ELISA titers and neutralization assay titers for polio virus type I. Unlike the presently described assays, however, the modified inhibition ELISA of Hagenaars et al. was more complex and cumbersome.

3. SUMMARY OF THE INVENTION

The present invention is based upon the surprising discovery that whole viruses, viral antigens and fragments thereof in which the structure of an oligosaccharide moiety of a viral glycoprotein has been "perturbed" are recognized more efficiently by serum, plasma or immunoglobulin fractions containing neutralizing antibody molecules. As used throughout the instant specification, the terms "perturbed" oligosaccharide and oligosaccharide "perturbation" are intended to encompass any modification (1) that alters the chemical or physical structure of a naturally occurring carbohydrate residue; (2) that removes, wholly or in part, a naturally occurring carbohydrate residue; and/or (3) that prevents or alters the addition of a carbohydrate residue to a virus, viral antigen of fragment thereof.

Any techniques known in the art for achieving such oligosaccharide "perturbations" including, but not limited to genetic engineering methods, are intended to fall within the scope of the present invention.

Based on this discovery, one embodiment of the present invention provides a novel method for detecting, as well as quantitating, the presence of virus neutralizing antibodies in samples of body fluids such as serum, plasma, various immunoglobulin fractions, etc. The novel method of the invention has the following advantages over conventional assays for neutralizing antibodies: (1) does not require use of cell culture techniques; (2) does not require use of infectious virus; (3) comprises a straight-forward serological assay; and (4) is complete in 4 hours or less. In contrast, conventional assays for virus neutralizing antibodies require: (1) cells in culture; (2) infectious virus; (3) skilled personnel; and (4) 5 days or so before an answer can be obtained. Thus, the present method is faster, easier and less complex than conventional methods. It does not require skilled personnel trained in the handling of infectious viral materials and is safer for use because even trained personnel need not be exposed to infectious virus.

Another embodiment of the present invention provides a novel method for preparing compositions comprising a virus, viral antigen or fragment thereof in which the oligosaccharide moiety is perturbed such that the compositions are useful for eliciting the formation of neutralizing antibodies. Thus these compositions provide vaccine formulations which stimulate an active immune response for prophylaxis of viral infections. For example, according to this embodiment a viral antigen is prepared having a perturbed oligosaccharide moiety and administered as a vaccine formulation to actively elicit the production of protective antibodies.

Another alternate embodiment of the present invention provides a variety of novel methods for preparing or identifying monoclonal or polyclonal neutralizing antibodies which can be administered to confer short-term passive immunity for prophylaxis and/or therapy of viral infections. For example, a perturbed viral antigen is used to identify those monoclonal antibodies prepared by hybridoma techniques which are capable of neutralizing virus. Such antibodies could be administered for prophylactic treatment of persons at risk of developing a particular viral disease.

The present invention may be more fully understood by reference to the following detailed description and examples of specific embodiments.

4. DETAILED DESCRIPTION OF THE INVENTION

The present invention relates to novel methods for diagnosis, prognosis, prophylaxis and therapy useful for a variety of viral infections. All the novel methods are based upon utilization of either whole virus, viral antigens or fragments of viral proteins in which "perturbation" of an oligosaccharide moiety renders the virus, viral antigen or fragment thereof more efficiently recognizable by neutralizing antibodies.

4.1. Oligosaccharide Perturbations

According to the present invention, oligosaccharide "perturbation" encompasses any modification (1) that alters the chemical or physical structure of a naturally occurring carbohydrate residue; (2) that removes, wholly or in part a naturally occurring carbohydrate residue; and/or (3) that prevents or alters the addition of a carbohydrate residue to a virus, viral antigen or fragment thereof. Illustrative examples of oligosaccharide perturbations include, but are not limited to the following.

Whole viruses, viral antigens or fragments thereof are perturbed by mild oxidation of an oligosaccharide moiety of a viral glycoprotein. For example, chemical oxidation of the oligosaccharide moiety can be accomplished using a variety of oxidizing agents such as periodic acid, paraperiodic acid, sodium metaperiodate, and potassium metaperiodate. Oxidation using such oxidizing agents is carried out by known methods. For a general discussion, see Jackson, in Organic Reactions 2, p. 341 (1944); Bunton, in Oxidation Chemistry, Vol. 1., Wiberg, ed., p. 367, Academic Press, New York (1944). The amount of the oxidizing agent depends on the kind of virus or viral antigen, but generally is used in excess of the amount of oxidizable oligosaccharide. The optimal amount can be determined by routine experimentation. The optimal ranges include: pH from about 4 to 8, a temperature range of about 0° to 37° C., and a reaction period of from about 15 minutes to 12 hours. During oxidation, light is preferably excluded from the reaction mixture in order to prevent over oxidation. Alternatively oxidation is achieved using an enzyme, such as galactose oxidase [Cooper et al., J. Biol. Chem. 234: 445–48 (1959)]. The influence of pH, substrate concentration, buffers and buffer concentration on the enzymatic oxidation are reported in Cooper et al., supra.

Whole viruses, viral antigens, or fragments thereof are perturbed by culturing virus infected cells in the presence of glycosylation inhibitors. For example, infected cells may be cultured in the presence of glycosylation inhibitors including, but not limited to: tunicamycin, streptovirudins, and/or glycosidase inhibitors such as carbohydrate analogs such as 2-deoxy-D-glucose and the like, and castanospermine, norjirimycin, 1-deoxynorjirimycin, bromocenduritol, 1-deoxymannojirimycin, and swainsonine, etc.

Whole viruses, viral antigens or fragments thereof are perturbed by enzymatically removing, either wholly or in part, a naturally occurring oligosaccharide moiety by exposing either virus infected cells in culture or isolated virus particles or fragments thereof to an enzyme which is specific for glycoside residues. Useful enzymes include neuraminidase, endo-beta-N-acetyglucosaminidases and the like.

Perturbation of viral antigens according to the present invention is also accomplished using genetic engineering techniques. For example, a gene encoding a particular viral-glycoprotein or fragment may be cloned and expressed in a bacterial organism. In such case, little to no glycosylation of the expressed viral protein occurs, resulting in a perturbed oligosaccharide. Alternatively, a gene encoding the desired viral glycoprotein or fragment can be cloned and expressed in a eukaryotic organism or cell culture. The eukaryotic organism or cell is then cultured in the presence of a glycosylation inhibitor such as tunicamycin or a glycosidase inhibitor such as castanospermine, norjirimycin, and the like resulting in expression of a protein or fragment having a perturbed oligosaccharide. Yet another alternative is to use site-selective mutagenesis techniques to alter a gene encoding a viral antigen or fragment in such a way as to remove or change the site(s) of glycosylation.

In case-s where the amino acid sequence of a viral glycoprotein or fragment is known, chemical methods of peptide synthesis provide yet another method for the preparation of a viral antigen or fragment thereof with a perturbed oligosaccharide.

The foregoing are merely illustrative examples of methods of oligosaccharide perturbation. Any other techniques known to those of skill in the art are intended to be encompassed by the perturbed oligosaccharide moiety.

The perturbed oligosaccharide of the virus, viral antigen or fragment thereof may be further modified, for example, by reduction with reducing agents such as sodium borohydride, cyanoborohydride and the like or by covalent attachment to a soluble or insoluble carrier or support.

4.2. Applications

The viruses, viral antigens and fragments thereof according to the present invention are advantageously used for methods suited for a number of different applications.

4.2.1. Diagnostic and Prognostic Applications

According to one embodiment of the invention, the virus, viral antigen or fragment thereof having a perturbed oligosaccharide moiety is used in a variety of methods for assaying a sample of body fluids such as serum, plasma or partially purified immunoglobulin fractions for the presence and titer of neutralizing antibodies.

The viruses, viral antigens or fragments thereof are used as ligands (antigens) to detect the presence of virus neutralizing antibodies in assay systems including but not limited to systems such as: Enzyme-Linked Immunosorbent Assays (ELISA), radioimmunoassays (RIA), immunofluoresence or other fluorescence-based assays, agglutination assays, etc. Examples of viruses for which neutralizing antibody titers are assayed would include those such as described in Section 4.3.

The titers obtained using assays with conventionally treated viruses, for example, conventional ELISA assays, which measure all antibodies, whether neutralizing or non-neutralizing, do not correlate with the titer determined in conventional virus neutralization assays. On the other hand, the titers obtained using the present viruses, viral antigens or fragments thereof having a perturbed oligosaccharide moiety (hereinafter referred to as a "perturbed antigen") have been found by Applicants to be significantly correlated with the titer of virus neutralizing antibodies, as determined by conventional virus neutralization assays. (See, for example, experimental results presented in Sections 5–7, infra). This may be due to a decrease in the binding of non-neutralizing antibody. Hence assays utilizing the present perturbed antigens are useful for diagnostic and/or prognostic prediction of the immuno-competent status of a patient with respect to a particular virus.

The method of the invention for detecting virus neutralizing antibodies in an aqueous sample comprises:

(a) contacting a ligand which comprises a virus, viral antigen or fragment thereof having a perturbed oligosaccharide moiety with an aqueous sample suspected of containing virus neutralizing antibodies in an assay system selected from the group consisting of an enzyme-linked immunosorbent assay, a radioimmunoassay, an agglutination assay, and an immunofluorescence assay and the like; and (b) detecting any reaction with the ligand; in which any reaction with the ligand indicates the presence of neutralizing antibodies in the sample. When quantitating the virus neutralizing antibodies is desired the method further comprises: comparing any reaction of ligand and antibodies to that of a standard.

4.2.1.1. Dissociation and Reassociation of Immune Complexes

Applicants anticipate that in certain instances, virus or virus fragments may be present in varying amounts in serum or plasma samples. These virus or virus fragments could be bound or associated with neutralizing and non-neutralizing antibodies in immune complexes. Consequently, the titer obtained using the present perturbed antigens in in vitro assays may be artifically low (i.e. false negatives). Hence, according to a further improved embodiment of the present invention, such immune complexes are dissociated prior to performing the diagnostic assays. Dissociation of immune complexes can be accomplished by methods known to those of skill in the art including but not limited to: use of chaotropic agents such as perchlorate ($ClO_4^-$), thiocyanate ($SCN^-$), etc., denaturing agents such as guanidine hydrochloride, urea, etc. and use of variation of pH, and the like. After dissociation, the liberated antibodies are contacted with perturbed antigens according to the present invention under conditons which permit association or reassociation with neutralizing antibodies.

4.2.2. Prophylactic and Therapeutic Applications

According to another embodiment of the present invention, the viruses, viral antigens and fragments thereof having a perturbed oligosaccharide moiety are used as immunogens in vaccine formulations to stimulate an active immune response in a vaccinated host.

When a whole virus having a perturbed oligosaccharide moiety is used, it is necessary to use either an attenuated or avirulent virus or an inactivated virus. An inactivated virus is obtained by treatment of a virus with various chemicals such as formaldehyde; then an oligosaccharide is perturbed using any of the methods described above in Section 4.1. Alternatively, an inactivated virus having a perturbed oligosaccharide moiety is obtained by chemical oxidation of a virus, for example, using periodic acid as described in Section 4.1. Such attenuated or inactivated viruses having a perturbed oligosaccharide moiety should induce antibodies that are more effective at neutralizing viral infections than conventionally attenuated or inactivated viruses.

Subunit vaccines containing only the necessary and relevant immunogenic material such as capsid glycoproteins of non-enveloped icosohedral viruses or the peplomers (glycoprotein spikes) of enveloped viruses or immunogenic fragments thereof can also be prepared in which the oligosaccharide moiety of the glycoprotein or fragment thereof is perturbed according to the present invention. Subunit vaccines can be prepared by isolating the relevant subunit from highly purified viral fractions or using recombinant DNA technology and perturbing the oligosaccharide moiety of the relevant immunogenic subunit as described in Section 4.1.

The vaccine formulations which stimulate an active immune response for prophylaxis of viral infections can be prepared by mixing the virus, viral antigen or fragment thereof having a perturbed oligosaccharide moiety in a carrier suitable for use in vivo. In order to enhance the immunological response of the host, the immunogenic virus, antigen or fragment thereof may be formulated with a suitable adjuvant. Suitable adjuvants include, but are not limited to: aluminum hydroxide, surface active substances, lysolecithin, pluronic polyols, polyanions, peptides including but not limited to muramyl peptides, and oil emulsions.

According to another alternate embodiment, a vaccine formulation to stimulate an active immune response for prophylaxis of viral infections is prepared by coupling a virus, viral antigen or fragment thereof having a perturbed oligosaccharide moiety to an immunogenic peptide or compound in order to enhance or potentiate the immunological response of the host.

According to yet another embodiment, the vaccine formulation can be prepared as a multivalent vaccine. To this end, a mixture of different viruses, viral antigens or fragments thereof each of which contains a perturbed oligosaccharide moiety and which is capable of eliciting an immune response against a different viral pathogen can be mixed together in one formulation.

Many methods can be used to introduce the vaccine formulations described above into a host. These include, but are not limited to: intradermal, intramuscular, intraperitoneal, intravenous, subcutaneous, and intranasal routes of administration.

According to another embodiment of the present invention, the viruses, viral antigens and fragments thereof having a perturbed oligosaccharide moiety are used in a variety of methods to prepare neutralizing antibodies which can be administered to confer short-term passive immunity for prophylaxis and/or therapy of viral infections. In one mode of this embodiment, a virus, viral antigen or fragment thereof having a perturbed oligosaccharide moiety is used as an immunogen in any technique that provides for the production of antibody molecules by continuous cell lines in culture. For example, the present immunogens can be utilized in the hybridoma methods originally developed by Kohler and Milstein, and reviewed by them in Sci. Amer. 243: 66–74 (1980) as well as in the human B-cell hybridoma methods described by Kozbor et al., Immunology Today 4: 72 (1983) and the EBV-hybridoma methods for producing human monoclonal antibodies described by Cole et al., in Monoclonal Antibodies and Cancer Therapy, Alan R. Liss, Inc., pp. 77–96 (1985) and the like. The monoclonal antibodies produced provide a readily available, consistent source of neutralizing antiboies specific for relevant virus which can be administered for passive immunization.

This embodiment of the invention encompasses a method for preparing a composition for administration to an animal or a human to confer short-term passive immunity or for prophylaxis or therapy of a viral-induced infection comprising: harvesting monoclonal antibodies produced by a hybridoma cell line formed by fusing a myeloma or hybridoma cell and a cell capable of producing antibody against a virus, viral antigen or fragment thereof having a pertrubed oligosaccharide moiety. It further encompasses a method for preparing a composition for administration to an animal or a human to confer short-term passive immunity or for prophylaxis or therapy of a viral-induced infection comprising: harvesting monoclonal antibodies produced by a lymphocyte cell line formed by transformation by an EBV virus of a mammalian lymphocyte cell capable of producing antibody against a virus, viral antigen or fragment thereof having a perturbed oligosaccharide moiety. Additionally it encompasses a method for preparing a composition for administration to an animal or a human to confer short-term passive immunity or for prophylaxis or therapy of a viral-induced infection comprising: (a) contacting a sample containing anti-viral antibodies with an antigen comprising a virus, viral antigen or fragment thereof having a perturbed oligosaccharide moiety to form an antibody-antigen complex; (b) separating the antibody-antigen complex from the sample; and (c) dissociating the antibody-antigen complex to obtain a purified antiviral antibody composition.

In another mode of this embodiment, a virus, viral antigen or fragment thereof having a perturbed oligosaccharide moiety is used in a screening assay to identify those viral-specific monoclonal antibodies which although known in the art have not been recognized as neutralizing antibodies. Hence this method screens for and identifies neutralizing monoclonal antibodies which can then be administered for passive immunization.

In yet another alternative mode of this embodiment of the present invention, a virus, viral antigen or fragment thereof is used to prepare neutralizing antibodies from serum, plasma or fractions of immunoglobulins derived therefrom. For example, a virus, viral antigen or fragment having a perturbed oligosaccharide moiety is immobilized and used in a preparative affinity chromatography format to isolate relevant neutralizing antibodies from serum or plasma by the formation of immune complexes. The polyclonal neutralizing antibodies are then separated from the immune complexes by conventional techniques.

The neutralizing antibodies which react specifically with the compositions of the present invention containing a perturbed oligosaccharide moiety can be formulated to confer short-term passive immunity to the host. Adjuvants are not needed in this type of preparation because the object is not to stimulate an immune response, but rather to inactivate or bind a viral pathogen. Thus, any suitable pharmaceutical carrier can be used. Passive immunization using such preparations can be utilized on an emergency basis for immediate protection of unimmunized individuals exposed to special risks of viral infections. Additionally, such preparations can be used prophylatically for viral infections such as measles and hepatitis.

In its most general form, the method of this embodiment of the invention encompasses a method for protection of an animal or a human from an infection induced by a virus, comprising: administering to an animal or human an effective amount of a vaccine formulation which comprises a virus, viral antigen or fragment thereof having a perturbed oligosaccharide moiety.

Such formulations can be administered to a host by routes including but not limited to: intradermal, intramuscular, intraperitoneal, intravenous and subcutaneous.

4.3. Viruses and Viral Antigens

The viruses, viral antigens and fragments thereof which are intended to be encompassed by the present invention include a wide variety of viruses such as DNA and RNA viruses including but not limited to retroviruses.

Specific examples include: DNA viruses such as: Adenoviridae such as adenoviruses subgroups B, C, D, E, F and G, etc; Herpesviridae such as herpes simplex I and II, cytomegalovirus, Epstein-Barr virus, varicella-zoster, etc.; Orthomyxoviridae such as influenza viruses, etc; Hepadnaviridae such as hepatitis B, hepatitis non-A, non-B, etc.; Parvoviridae such as parvoviruses, etc.; RNA viruses such as Togaviridae such as rubella, etc.; Paramyxoviridae such as measeles, parainfluenza, respitatory syncytial virus, etc.; Flaviviridae such as dengue virus types 1–4, yellow fever virus, tick-borne fever viruses, etc.; Rhabdoviridae such as rabies, vesicular stomatitis virus, Marburg-Ebola virus, etc.; Bunyaviridae such as Rift Valley Fever, California encephalitis virus group, sand fly fever virus, etc.; Arenaviridae such as Lassa fever virus, Junin virus, lymphocytic choriomeningitis virus, etc.; Reoviridae such as rotovirus, etc.; Picornaviridae such as polio virus, coxsackieviruses, hepatitis A virus, rhinovirus, etc.; Retroviridae such as human lymphoadenopathy-associated virus (LAV, HIV, HTLV-III), human T-cell lymphotrophic virus types I, II, III, feline leukemia virus, etc.

The following Examples are given for the purpose of illustration and not by way of limitation on the scope of the invention.

In the ELISA assays described below in which the virus was covalently attached to the microtiter plate, the microtiter plates were pre-saturated using either 200 ul of 0.5% calf IgG in 0.14 M NaCl or 300 ul of 0.5% bovine serum albumin in 0.5 M Tris-citrate buffer containing 0.1% Tween-20, pH 8.1 in order to eliminate the non-specific adsorption of virus or serum proteins or IgG. In the ELISA assays described below in which the virus was attached to the plate via adsorption, the virus was allowed to adsorb to the plate and then the plates were saturated using either calf IgG in 0.14 M NaCl or bovine serum albumin in 0.5 M Tris-citrate buffer.

5. EXAMPLES: DETERMINATION OF NEUTRALIZING ANTIBODIES IN PURIFIED HUMAN IgG FROM SERA

5.1. Detection of Neutralizing Anti-CMV Antibodies in Human IgG

The following series of experiments demonstrate that ELISA assays in which the oligosaccharide moiety of the viral antigen was perturbed according to the present invention are useful for determining the titer of virus-neutralizing antibodies. In contrast, conventional ELISA assays in which the virus was either adsorbed or covalently attached without perturbation of the oligosaccharide moiety are not.

The antigen used in the assays was whole cytomegalovirus (CMV) obtained from homogenates of cultured human fibroblast cells ($MRC_5$) infected with CMV for six to eight days. The microtiter wells containing an equivalent amount (about 1 ug/well) of CMV were prepared for the various ELISA assays as follows:

(A) ELISA'S Using Antigen With Perturbed Oligosaccharide.

(1) Virus Covalently Attached Via Oxidized Oligosaccharide Moiety:

The carbohydrate moiety of CMV was oxidized using sodium periodate ($NaIO_4$) as described in Section 4 and covalently coupled to a reactive amine on a side chain of the polyhydrazidostyrene of the well. Addition of a reactive amine group to polystyrene (or the microtiter well) was carried out by the method of Chin and Lanks [Anal. Biochem, 83: 709–19 (1977)]. Polystrene was first converted to nitrostyrene which was then reduced to aminostyrene. Polyaminostyrene was then converted to polyhydrazidostyrene in a two-step process: (1) polyaminostyrene was succinylated; and then (2) an amide bond was formed betwen hydrazine and the succinylated polyaminostyrene using carbodiimide. (Ox Oligosaccharide Attached ELISA).

(2) Virus Covalently Attached Via Amine Group, Oxidized Oligosaccharide Moiety:

The CMV virus was covalently attached to the polycarbostyrene via a peptide bond formed using carbodiimide to couple an amine residue of the virus to an activated carboxyl of the polycarbostyrene. The carbohydrate moiety of the virus was then oxidized in situ using $NaIO_4$ as described in Section 4. (Amine Attached Oligosaccharide Ox ELISA).

(B) Conventional ELISA'S Using Antigen with Non-Perturbed Oligosaccharide.

(1) Virus Covalently Attached Via Amine Group:

CMV was attached using carbodiimide to form a peptide bond between an amine group of an amino acid residue of the virus and a free carboxyl group of a polycarbostyrene of the well. (Amine Attached ELISA).

(2) Virus Non-Covalently Attached:

CMV was simply non-covalently fixed by adsorption onto a non-modified polystyrene well. (Adsorption ELISA).

Partially purified human IgG was obtained from human serum samples using conventional ammonium sulfate precipitation techniques. After precipitation, the tubes were centrifuged at 12,000 rpm for 5 minutes. The supernatant was discarded, the pellet was washed, recentrifuged and resuspended in 0.14 M NaCl. The partially purified human IgG samples were serially diluted in Buffer I of the following composition:

| | |
|---|---|
| Calf IgG | 0.5% |
| NaCl | 0.14 M |
| Glycine | 0.1 M |
| Sodium borate | 0.05 M |
| Synperonic PE/L62 | 0.10% (v/v), | adjusted to pH 8.1 with 1.0 M HCl. 100 ul of each dilution was distributed in the wells of the plate containing the CMV. After two hours incubation at 37° C., the plates were washed in the Buffer I, but without calf IgG.

Then 100 ul of a goat serum solution containing anti-human IgG labeled with alkaline phosphatase, diluted to 1/1000 in the following Buffer II, was introduced into each well:

| | |
|---|---|
| Bovine serum albumin | 1.0% |
| NaCl | 0.14 M |
| Glycine | 0.1 M |
| Borate | 0.05 M |
| Synperonic PE/L62 | 0.10% (v/v) |

After a contact time of one hour at 37° C., the wells were washed with Buffer II but without bovine serum albumin (BSA). The enzymatic activity was determined at 37° C. using p-nitrophenyl phosphate as substrate at a concentration of 0.2% (p/v) dissolved in a buffer containing: 2-amino-2-methyl-1-propanol (0.625 M) and $MgCl_2$ (2.0 mM), pH 10.25. The optical density was measured at 405 nm either every five minutes during a period of 30 minutes or after 30 minutes of incubation.

A conventional CMV infective power neutralization assay was performed using $MRC_5$ cells in culture as described by Krech et al., Z. Immun.-Forsch, Bd. 141S: 411-29 (1971).

Results are illustrated in Table 1. The antibody titer obtained using the ELISA assays and the conventional virus neutralization assays were calculated as a protein concentration of 1 mg/ml of non-diluted IgG sample. Table 2 presents the linear correlation coefficients obtained when the titers obtained by the various assays were compared.

TABLE 1

TITERS OF CMV-NEUTRALIZING ANTIBODIES IN PURIFIED IgG

| IgG Sample | Neutralization Titer | Ox Oligosaccharide Attached ELISA Titer | Amine Attached Oligosaccharide Ox ELISA Titer | Amine Attached ELISA Titer | Adsorption ELISA Titer |
|---|---|---|---|---|---|
| 1 | 128 | 50 | <50 | 400 | 67 |
| 2 | 256 | 50 | <50 | 200 | 144 |
| 3 | 256 | 100 | 100 | 400 | 519 |
| 4 | 512 | 400 | 100 | 800 | 1087 |
| 5 | 64 | <50 | <50 | 50 | 54 |
| 6 | 128 | 50 | 50 | 200 | 67 |
| 7 | 256 | 200 | 200 | 800 | 432 |
| 8 | 465 | 364 | 181 | 727 | 2780 |
| 9 | 621 | 485 | 485 | 485 | 1005 |
| 10 | 512 | 400 | 400 | >1600 | 2923 |
| 11 | 128 | 200 | 100 | 400 | 387 |
| 12 | 256 | 100 | 100 | 1600 | 593 |
| 13 | 64 | <50 | 50 | 54 | 100 |
| 14 | 256 | 50 | 50 | 455 | 400 |

TABLE 2

COMPARISONS OF ASSAYS FOR CMV-NEUTRALIZING ANTIBODIES

| Assay | Linear Correlation Coefficients | | | | |
|---|---|---|---|---|---|
| Neutralization | 1 | | | | |
| Adsorption ELISA | 0.74 | 1 | | | |
| Ox Oligosaccharide Attached ELISA | 0.90 | 0.75 | 1 | | |
| Amine Attached ELISA | 0.52 | 0.62 | 0.41 | 1 | |
| Amine Attached Oligosaccharide Ox ELISA[a] | 0.78 (0.87) | 0.65 (0.64) | 0.82 (0.93) | 0.46 (0.48) | 1 |
| | Neutralization | Adsorption ELISA Attached | Ox Oligosaccharide ELISA | Amine Attached ELISA | Amine Attached Oligosaccharide |

TABLE 2-continued

COMPARISONS OF ASSAYS FOR CMV-NEUTRALIZING ANTIBODIES

| Assay | Linear Correlation Coefficients |
| --- | --- |
| | Ox ELISA |

[a]The number in parentheses represents the correlation coefficient obtained when one aberrant titer value was discarded.

As demonstrated in Tables 1 and 2, the titer obtained using ELISA assays according to the present invention, i.e., the Ox Oligosaccharide Attached ELISA and the Amine Attached oligosaccharide Ox ELISA was highly positively correlated with the titer obtained using the conventional neutralization Assay (correlation coefficients, respectively: 90 and 0.87). On the other hand, the titer obtained using the conventional Amine Attached ELISA showed no significant correlation with the titer of neutralizing antibody (correlation coefficient: 0.52). The Amine Attached ELISA showed much weaker, non-significant correlation with titer of neutralizing antibody (correlation coefficient: 0.74).

Table 2 demonstrates further that there was a significant positive correlation between the titer obtained using the Ox Oligosaccharide Attached ELISA and the Amine Attached Oligosaccharide Ox ELISA (correlation coefficient: 0.93). At the same time, however, there was no significant correlation observed between the titers obtained using the Adsorption ELISA and the Amine Attached Oligosaccharide Ox ELISA, or the Amine Attached Oligosaccharide Ox ELISA and the Amine Attached ELISA. This indicates that the significant correlation observed between the titers of neutralizing antibody using the Neutralization Assay and both the Amine Attached Oligosaccharide Ox ELISA and the Ox Oligosaccharide Attached ELISA is not related to the method of covalent attachment, but rather may be related to the perturbation of the oligosaccharide moiety achieved by oxidation. Moreover, these results suggest further that it does not matter whether the oligosaccharide perturbation occurs prior to or following covalent attachment of the virus to the microtiter well.

5.2. Reproducibility of Neutralizing Antibody Titer

The following experiment demonstrates the reproducibility of results obtained using an ELISA assay in which the virus was covalently attached to a insoluble support via an oxidized carbohydrate moiety of the virus.

A series of ELISA assays to determine the titer of neutralizing anti-CMV antibodies was performed as described in Section 5.1 in which CMV was covalently attached to a reactive amine on a side chain of an insoluble support via an oxidized carbohydrate moiety of the CMV antigen. The samples used were purified IgG obtained from the same serum samples used for the experiments described in Section 5.1. One set of ELISA's were performed on one aliquot of purified IgG's, and a duplicate set of assays were performed on another aliquot of the same IgG's some 17½ months later. The samples were stored frozen at −70° C. during the interim. Results are presented in Table 3.

TABLE 3

REPRODUCIBILITY OF CMV NEUTRALIZING ANTIBODY ASSAY

| Sample No. | Antibody Titer - ELISA Virus Covalently Attached Via Oxidized Oligosaccharide | |
| --- | --- | --- |
| | Experiment 1 | Experiment 2 |
| 1 | 50 | 40 |
| 2 | 50 | 40 |
| 3 | 100 | 160 |
| 4 | 400 | 320 |
| 5 | <50 | 160 |
| 6 | 50 | 40 |
| 7 | 200 | 160 |
| 8 | 364 | 290 |
| 9 | 485 | 388 |
| 10 | 400 | 640 |
| 11 | 200 | 160 |
| 12 | 100 | 80 |
| 13 | <50 | 80 |
| 14 | 50 | 80 |

As demonstrated in Table 3, the results of antibody titers obtained using the ELISA assay in which the virus was covalently attached via a perturbed oligosaccharide moiety are highly reproducible.

6. EXAMPLE: DETECTION OF NEUTRALIZING ANTIBODIES IN SERUM SAMPLES

The following series of assays demonstrate that an ELISA assay in which the oligosaocharide moiety of a virus antigen was perturbed is useful for determining the titer of neutralizing antibody in human serum samples.

An ELISA assay was performed as described in Section 5.1 in which the oligosaccharide moiety of the CMV virus was oxidized and covalently coupled to a hydrazido group on the polyhydrazidostyrene of the microtiter well. A conventional ELISA assay was performed as described in Section 5.1 in which the CMV was merely adsorbed to the microtiter well. A virus neutralization assay as described in Section 5.1 was also performed.

Results of all three assays are compared in Table 4.

TABLE 4

| Serum Sample No. | Adsorption ELISA Titer[a] | Neutralization Assay Titer | Oxidized Oligosaccharide Attached ELISA Titer[b] |
| --- | --- | --- | --- |
| 1 | 6400 | 160 | 125 |
| 2 | 26600 | 320 | 250 |
| 3 | 102400 | 640 | 2000 |
| 4 | 25600 | 640 | 1000 |
| 5 | 102400 | 2560 | 4000 |
| 6 | 25600 | 2560 | 4000 |

[a]Correlation coefficient between Neutralization Assay Titer and Adsorption ELISA Titer: +0.37.
[b]Correlation coefficient between Neutralization Assay Titer and Oxidized Oligosaccharide Attached ELISA Titer: +0.96.

As demonstrated in Table 4, there was a highly significant positive correlation between the titer of antibodies in human serum samples measured by the Neutralization Assay and by an ELISA assay in which the oligosaccharide moiety of CMV was oxidized and covalently coupled to the microtiter well. Thus using polyclonal sera, this ELISA assay is "predictive" of the immunocompetent status of the patient. In contrast, no correlation was observed between the antibody titer measured by the Neutralization Assay and that obtained using a conventional ELISA in which non-perturbed CMV virus was merely adsorbed to the microtiter well

7. EXAMPLE: PERTURBATION OF OLIGOSACCHARIDE MOIETY OF VIRUS AND ATTACHMENT OF VIRUS TO A SOLID SUPPORT

As suggested by results presented in Section 5.1 above, when a perturbed antigen is used to determine the titer of neutralizing antibodies in an ELISA format in which the antigen is covalently attached to the microtiter well, it does not matter whether the oligosaccharide moiety is perturbed before or after covalent attachment to the microtiter well. The following series of experiments was performed to investigate the effect of perturbation of the oligosaccharide moiety according to the present invention upon the ability of the virus to attach to a microtiter plate.

The oligosaccharide moiety of CMV virus was perturbed by oxidization using $NaIO_4$ for 16 hours at 4° C. as described in Section 4. ELISA assays for anti-CMV antibodies were conducted as described in Section 5.1,. in which: (1) CMV having a perturbed oligosaccharide moiety in PBS was adsorbed to a polystryrene microtiter plate. (2) CMV having a perturbed oligosaccharide moiety was covalently coupled via the carbohydrate moiety to a reactive amine group of a polyhydrazidostyrene microtiter plate in the presence of phosphate buffer containing 0.1% Tween-20 (PBT). PBT was used to prevent non-covalent adsorption of CMV to the polyhydrazidostyrene plate. (3) Non-perturbed CMV in PBS was adsorbed to a polystyrene microtiter plate.

Results are illustrated in Table 5.

TABLE 5

COMPARISON OF ELISA TITERS OF CMV WITH PERTURBED AND NON-PERTURBED OLIGOSACCHARIDE

| IgG No. | Ox CMV Adsorbed in PBS[a] | Ox CMV Covalently in PBT[b] | Non-Ox CMV Adsorbed in PBS[a] |
|---|---|---|---|
| Y 287 | 4000 | 4000 | 8000 |
| Y1096 | 1000 | 1000 | 8000 |

[a]CMV either native or having a perturbed oligosaccharide moiety in PBS (phosphate buffer saline, pH 7.4) was immobilized by adsorption onto polystyrene microtiter plates.

[b]CMV having a perturbed oligosaccharide moiety in PBT (50 mM phosphate buffer, 0.1% Tween-20, pH 6.0) was covalently coupled to polyhydrazidostyrene of microtiter plates.

As demonstrated in Table 5, there was no difference in ELISA titers obtained in which a perturbed antigen was either covalently attached or merely adsorbed to the micro-titer well. When the perturbed CMV was incubated in the microtiter wells in the presence of PBT, the titer obtained was zero because the perturbed virus does not adsorb in the presence of Tween-20 (results not shown).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method for detecting virus neutralizing antibodies in an aqueous sample, comprising:

(a) contacting (i) a ligand which comprises a virus, viral antigen or fragment thereof, said virus, viral antigen or fragment thereof having perturbed oligosaccharide moiety, in which said perturbed oligosaccharide moiety was obtained by oxidation, by means of an agent selected from the group consisting of periodic acid, salts thereof, paraperiodic acid, salts thereof, metaperiodic acid, salts thereof, and oxidase enzymes, of an unperturbed oligosaccharide moiety, with (ii) an aqueous sample suspected of containing virus neutralizing antibodies in an assay system selected from the group consisting of an enzyme-linked immunosorbent assay, a radioimmunoassay, an agglutination assay, and an immunofluorescence assay; and (b) detecting any reaction with the ligand; in which any reaction with the ligand indicates the presence of neutralizing antibodies in the sample.

2. A method for detecting and quantitating virus neutralizing antibodies in an aqueous sample, comprising:

(a) contacting (i) a ligand which comprises a virus, viral antigen or fragment thereof, said virus, viral antigen or fragment thereof having a perturbed oligosaccharide moiety, in which said perturbed oligosaccharide moiety was obtained by oxidation, by means of an agent selected from the group consisting of periodic acid, salts thereof, paraperiodic acid, salts thereof, metaperiodic acid,.salts thereof, and oxidase enzymes, of an unperturbed oligosaccharide moiety, with (ii) an aqueous sample suspected of containing virus neutralizing antibodies in an assay system selected from the group consisting of an enzyme-linked immunosorbent assay, a radioimmunoassay, an agglutination assay, and an immunofluorescence assay;

(b) detecting any reaction with the ligand; in which any reaction with the ligand indicates the presence of neutralizing antibodies in the sample; and (c) comparing any reaction of ligand and antibodies to that of a standard.

3. The method according to claim 1 or 2, in which the sample is an aliquot of a body fluid.

4. The method according to claim 3, in which the body fluid is serum or plasma.

5. The method according to claim 1 or 2, in which the aqueous sample is an aliquot of a solution of a monoclonal antibody.

6. The method according to claim 1 or 2, in which the virus neutralizing antibodies neutralize a virus selected from the group consisting of: adenoviridae, herpesviridae, orthomyxoviridae, hepadnaviridae, parvoviridae, togaviridae, paramyxoviridae, flaviviridae, rhabdoviridae, bunyviridae, reoviridae, picornaviridiae and retroviridae.

7. The method according to claim 1 or 2, in which the virus neutralizing antibodies neutralize cytomegalovirus.

8. The method according to claim 1 or 2 in which the virus neutralizing antibodies neutralize herpes simplex I or herpes simplex II virus.

9. The method according to claim 1 or 2, in which the virus neutralizing antibodies neutralize hepatitis virus.

10. The method according to claim 1 or 2, in which the virus neutralizing antibodies neutralize rubella virus.

11. The method according to claim 1 or 2, in which the virus neutralizing antibodies neutralize measles virus.

12. The method according to claim 1 or 2, in which the virus neutralizing antibodies neutralize parainfluenza virus.

13. The method according to claim 1 or 2, in which the virus neutralizing antibodies neutralize dengue virus.

14. The method according to claim 1 or 2, in which the virus neutralizing antibodies neutralize human lymphadenopathy-associated virus (LAV, HTLV-III, HIV).

15. The method according to clain: 1 or 2, further comprising the step of dissociating any immune complexes which may be present in the aqueous sample prior to contacting the ligand with the sample.

16. The method according to claim 1 or 2, in which the aqueous sample contains artially purified immunoglobulin.

17. A method for detecting virus neutralizing antibodies in an aqueous sample, comprising:
(a) contacting a virus, viral antigen or fragment thereof with oxidizing agent selected from the group consisting of periodic acid, salts thereof, paraperiodic acid, salts thereof, metaperiodic acid, salts thereof, and oxidase enzymes to form a ligand which comprises a virus, viral antigen or fragment thereof, said virus, viral antigen or fragment thereof having a perturbed oligosaccharide moiety;
(b) contacting the ligand with an aqueous sample suspected of containing virus neutralizing antibodies in an assay system selected from the group consisting of an enzyme-linked immunosorbent assay, a radioimmunoassay, an agglutination assay, and an immunofluorescence assay;
(c) detecting any reaction with the ligand; in which any reaction with the ligand indicates the presence of neutralizing antibodies in the sample.

18. The method according to claim 17, which further comprises:
(d) comparing any reaction of the ligand and antibodies to that of a standard in order to quantitate the virus neutralizing antibodies.

* * * * *

UNITED STATES PATENT AND TRADEMARK OFFICE
CERTIFICATE OF CORRECTION

PATENT NO. : 4,853,326

DATED : August 1, 1989

INVENTOR(S) : Gerard A. Quash, et. al.

It is certified that error appears in the above-indentified patent and that said Letters Patent is hereby corrected as shown below:

On the Title page, item [73], Assginee: add Institut National de la Sante et de la Recherche Medicale Paris, France.

Signed and Sealed this

Twenty-eighth Day of June, 1994

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 4,853,326

DATED : August 1, 1989

INVENTOR(S) : Gerard A. Quash, John D. Rodwell, Thomas J. McKearn and Jean Pierre Ripoll It is certified that error appears in the above-identified patent and that said Letters Patent is hereby corrected as shown below:

On the title Page:

[73]  Add to Assignee:
      Institut National de la Sante et de la Recherche Medicale
      Paris, France.

Signed and Sealed this

Thirteenth Day of September, 1994

Attest:

BRUCE LEHMAN

Attesting Officer

Commissioner of Patents and Trademarks